(12) United States Patent
Chen et al.

(10) Patent No.: US 11,826,453 B2
(45) Date of Patent: Nov. 28, 2023

(54) HAIR CARE COMPOSITION COMPRISING PIROCTONE OLAMINE

(71) Applicant: Conopco, Inc., Englewood Cliffs, NJ (US)

(72) Inventors: Guoqiang Chen, Shanghai (CN); Yudong Wang, Shanghai (CN)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 17/610,208

(22) PCT Filed: May 4, 2020

(86) PCT No.: PCT/EP2020/062230
§ 371 (c)(1),
(2) Date: Nov. 10, 2021

(87) PCT Pub. No.: WO2020/229203
PCT Pub. Date: Nov. 19, 2020

(65) Prior Publication Data
US 2022/0218581 A1    Jul. 14, 2022

(30) Foreign Application Priority Data

May 14, 2019  (WO) ............... PCT/CN2019/086898
Jun. 17, 2019  (EP) .................................. 19180528

(51) Int. Cl.
| A61Q 5/02 | (2006.01) |
| A61Q 5/12 | (2006.01) |
| A61K 8/49 | (2006.01) |
| A61Q 5/00 | (2006.01) |

(52) U.S. Cl.
CPC ............ *A61K 8/4926* (2013.01); *A61Q 5/006* (2013.01); *A61Q 5/02* (2013.01); *A61Q 5/12* (2013.01); *A61K 2800/596* (2013.01)

(58) Field of Classification Search
None
See application file for complete search history.

(56) References Cited

U.S. PATENT DOCUMENTS

| 3,644,626 A | 2/1972 | Witzel |
| 3,655,897 A | 4/1972 | Witzel |
| 3,754,088 A | 8/1973 | Witzel |
| 4,451,469 A | 5/1984 | Singh et al. |
| 4,540,699 A | 9/1985 | Brown et al. |

FOREIGN PATENT DOCUMENTS

| CN | 103442681 | 12/2013 |
| CN | 105748376 | 7/2016 |
| CN | 106832439 | 6/2017 |
| CN | 107875030 | 4/2018 |
| DE | 102007045241 | 10/2008 |
| EP | 0034385 | 8/1981 |
| EP | 0173259 | 3/1986 |
| JP | 63179813 | 7/1988 |
| WO | WO9966886 | 12/1999 |
| WO | WO00067699 | 11/2000 |
| WO | WO-2012022552 A1 * | 2/2012 | ............... A61K 8/27 |
| WO | WO2016058837 | 4/2016 |
| WO | WO-2018172121 A1 * | 9/2018 | ............... A61K 8/27 |

OTHER PUBLICATIONS www.in-cosmetics.com/_novadocuments/2882; Pirontone Olamine; Spec-Chem Ind XP055625058; Sep. 23, 2009; www.in-cosmetics.com.
Search Report and Written Opinoin in EP19180529; dated Nov. 21, 2019.
Gilbert a Youngdale et al; 1,2-Dihydro-2-oxo-6-(2,2-dimethylpropyl) 3-pyridinecarboxylic acid, "A new class of oral hypoglycemic agents" Analogues, and derivatives; J. Med. Chem; Jan. 1, 1985; 1790-1796 (also as XP055638504); 28.
Search Report and Written Opinoin in EP19180528; dated Nov. 21, 2019.
Clariant; Antidandruff Active Ingredient Octopirox; XP055319009; Jun. 11, 2015; pp. 1-16.
J Streith et al; XP055639159; Tetrahedron Letters; Jan. 1, 1966; 1348, 1349.
Spec-Chem Ind; XP055625058; Spec-Chem Ind: "Pirontone Olamine"; Sep. 23, 2009; 3,6,8; www.in-cosmetics.com/_novadocuments/2882.
Clariant; Antidandruff Active Ingredient Octopirox, Salzbach; XP055319009; Jun. 11, 2015; 9,13,14; www.myskinrecipes.com/shop/atta.
Search Report and Written Opinion in PCTEP2020062230; Jul. 29, 2020.
Search Report and Written Opinion in PCTEP2020062130; Jul. 29, 2020.
Streith, J., et al.; Reactions photoinduites de N-oxydes d'heterocycles aromatiques azotes IV (1,2,3), photochimie des pyridine-N-oxydes (4). [Photoreactions of aromatic nitrogenous heterocycle n-oxide (4); Bulletin De La Societe Chimique De France; 1970; pp. 1157-1167 (also as XP009516933); No. 3; France.

(Continued)

*Primary Examiner* — Jyothsna A Venkat
(74) *Attorney, Agent, or Firm* — Stephanie S. DelPonte

(57) ABSTRACT

Disclosed is a hair care composition comprising a compound of the formula (1) and a photolabile antidandruff agent wherein said photolabile antidandruff agent is piroctone olamine. The compound of formula (1), which is a 2(1H)-pyridinone, may be a degradation product of piroctone olamine on exposure to UV radiation and has been shown to improve the stability of piroctone olamine.

Formula (1)

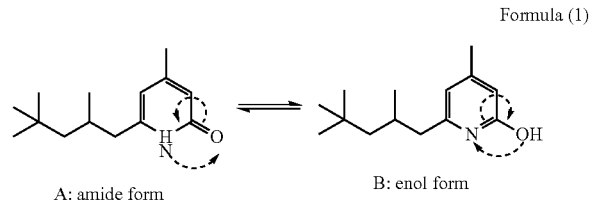

A: amide form       B: enol form

13 Claims, No Drawings

(56) References Cited

OTHER PUBLICATIONS

Gagliardi, L., et al.; "HPLC Determination of Ciclopirox, Octopirox, and Pyrithiones in Pharmaceuticals and Antidandruff Preparations"; Journal of Liquid Chromatography & Related Technologies; 21(15); pp. 2365-2373; 1998.

Zhang, Q.; "Detection method of common anti-dandruff agent in cosmetics"; China Pharmaceuticals; 23(20); pp. 122-123; 2014.

* cited by examiner

HAIR CARE COMPOSITION COMPRISING PIROCTONE OLAMINE

CROSS REFERENCE TO RELATED APPLICATIONS

The present application is a U.S. National Phase Application under 35 U.S.C. § 371 of International Application No. PCT/EP2020/062230, filed on May 4, 2020, which claims priority to International Application No. PCT/CN2019/086898 filed on May 14, 2019, and European patent application No. 19180528.2 filed on Jun. 17, 2019, the contents of which are incorporated herein in their entireties.

FIELD OF THE INVENTION

The present invention relates to hair care compositions. More particularly the invention relates to hair care compositions that comprise piroctone olamine.

BACKGROUND OF THE INVENTION

Dandruff is a condition experienced by many people worldwide. The dandruff condition varies from mild symptoms such as flaking skin to severe inflammation and itchiness of the scalp. *Malassezia* yeasts, such as *Malassezia furfur*, are believed by some to be the main cause of dandruff and, whilst this might not represent the full scientific picture of the situation, *Malassezia* yeasts do appear to be closely associated with dandruff. Hence, the strategy conventionally used for the treatment of dandruff is the topical application of antifungals such as zinc pyrithione (ZnPTO), piroctone olamine, climbazole and ketoconazole which are normally delivered through a shampoo.

Piroctone olamine (also known as Octopirox®) is a compound often used in the treatment of fungal infections. Piroctone olamine is the ethanolamine salt of the hydroxamic acid derivative piroctone. Piroctone olamine has anti-fungal properties that make it ideal for controlling the root cause of dandruff, a commonly occurring fungus called *Malassezia globosa*. It is often used in anti-dandruff shampoo as a replacement for the commonly used compound zinc pyrithione. Generally, piroctone olamine is dissolved in the base composition of a shampoo which includes surfactants, water, silicones, polymers and colouring and fragrance ingredients. When a user applies the compositions to hair and scalp, some compound of piroctone olamine get deposited thereon.

Generally, efficacy of an antidandruff shampoo or conditioner depends on the amount of antidandruff active deposited on the scalp and hair because more deposition means more bioavailability. However, it is well known that piroctone olamine is light instable and the piroctone olamine that is deposited is not bioavailable as piroctone olamine tends to react with UV radiation which leads to its destabilization. This destabilization can be avoided to some extent by using UV photostabilisers or sunscreens. Efforts have also been made to increase the antimicrobial efficacy of piroctone olamine by combining it with "booster" technologies.

Introduction of piroctone olamine from Spec-Chem Ind. discloses hair care compositions comprising piroctone olamine and the antidandruff and antimicrobial efficacy of piroctone olamine.

Introduction of antidandruff active ingredient Octopirox® from Clariant discloses that the octopirox is unstable under light. It also discloses the compositions comprising octopirox and the production of octopirox.

DE 102007045241A1 (Beiersdorf AG) discloses cosmetic or dermatological preparation comprising one or more piroctone olamines and one or more stabilizing agents selected from the group of benzaldehydes and/or alkanediols and/or triols.

SUMMARY OF THE INVENTION

The present inventors have determined a new way of improving the problem of photo stability of a photolabile antidandruff agent such as piroctone olamine. We have determined that photo stability of piroctone olamine can be improved if piroctone olamine and a new compound which is one of degradation products of piroctone olamine are co-formulated into a composition. Piroctone olamine is prone to degradation upon sustained exposure to UV radiation. When piroctone olamine degrades, it is no longer as effective.

In accordance with a first aspect, disclosed is a hair care composition comprising:
 (i) a compound of the formula 1, which may exist in amide form A or enol form B;

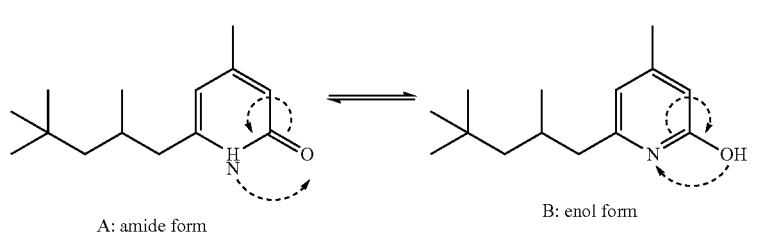

Formula 1

A: amide form

B: enol form (ii) a photolabile antidandruff agent; and
 (iii) a cosmetically acceptable carrier; wherein said photolabile antidandruff is piroctone olamine.

In accordance with a second aspect, disclosed is a non-therapeutic method of treating dandruff comprising a step of applying thereon a composition of the first aspect.

DETAILED DESCRIPTION OF THE INVENTION

For the avoidance of doubt, any feature of one aspect of the present invention may be utilized in any other aspect of the invention. The word "comprising" is intended to mean "including" but not necessarily "consisting of or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description and claims indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated. As used herein, the indefinite article "a" or "an" and its corresponding definite article "the" means at least one, or one or more, unless specified otherwise. The various features of the present invention referred to in individual sections above apply, as appropriate, to other sections mutatis mutandis. Consequently, features specified in one section may be combined with features specified in other sections as appropriate. Any section headings are added for convenience only, and are not intended to limit the disclosure in any way.

By "hair care composition" as used herein, is meant to include a composition for topical application to hair or scalp of mammals, especially humans. By topical is meant that the composition is applied to the external surface of the body. In the present invention this is achieved by applying the composition on the hair or scalp. Such a composition may be generally classified as leave-on or rinse off, and includes any product applied for improving the appearance, cleansing, odor control or general aesthetics of scalp and hair. The haircare composition of the present invention could be in the form of a liquid, lotion, cream, foam, scrub, gel, shampoo, conditioner, shower gel or bar. The haircare composition of the present invention is preferably a leave-on composition. Alternatively, the haircare composition of the present invention is a wash-off composition. Compositions for achieving the desired benefits by way of ingestion into the human body are excluded from the scope of the present invention.

Compound of the Formula 1

The composition in accordance with this invention comprises a compound of the formula 1, which may exist in amide form A or enol form B:

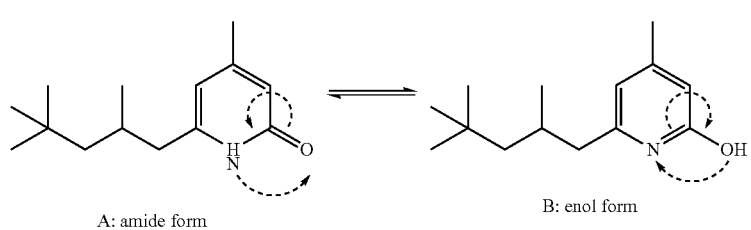 [SMILES: Cc1cc(CC(C)CC(C)(C)C)[nH]c(=O)c1 ; Cc1cc(O)nc(CC(C)CC(C)(C)C)c1]

A: amide form

B: enol form

Formula 1

The pH of the composition can impact the structure of the compound of the formula 1. The amide form dominates when the pH is below 7, and it is enol form dominates when the pH is greater than 7.

The compound of formula 1 can be produced by a process comprising the steps of:
i) preparing a solution of piroctone olamine by dissolving piroctone olamine in an organic solvent or in water comprising at least one surfactant;

ii) exposing said solution to UV light of 100 mW to 2000 mW in a UV chamber for 0.5 hour to 8 hours to cause degradation of piroctone olamine to form degradation products of said piroctone olamine;
iii) separating said degradation products of piroctone olamine to a chromatographic technique to get said compound of the formula 1.

In step ii), the time of exposing said solution under UV radiation depends on the intensity of UV radiation. The intensity of UV radiation has to be at least 100 mW. When it's exposed under UV light of 100 mW, it needs about 8 hours.

It is preferred that the organic solvent of step i) is an alcohol. It is more preferred that the organic solvent of step i) is methanol or ethanol.

It is preferred that the aqueous surfactant solutions of step i) comprise an anionic surfactant or a non-ionic surfactant.

It is preferred that the chromatographic technique used in step iii) is selected from Preparation Liquid Chromatography (pre-LC) with a Preparative LC column, or column chromatography, or Thin Layer Chromatography (TLC).

It is particularly preferred that the method used to separate the degradation products is preparation liquid chromatography (pre-LC) with a preparative LC column (Shiseido, 20*250 mm, 5 μm). A preferred method is described below:

The column is eluted with methanol and water at a flow rate of 15 mL/minute (5 mL/minute for second purification). The eluent is consecutively collected into a series of sample tubes (15 mL/tube). After separated by preparative chromatography, the eluent solution in each sample tube is analyzed using a HPLC-UV. The eluent solution tubes which were confirmed to contain the compound of formula 1 are collected and dried to get the compound of formula 1 in powder form.

Preferably, the hair care composition of the present invention comprises the compound of formula 1 in an amount of from 0.01 to 10 wt %, more preferably 0.1 to 5 wt %, furthermore preferably from 0.5 to 2.5 wt % by weight of the composition.

Photolabile Antidandruff Agent

Photolabile means the agent is susceptible of undergoing photochemical reactions under the influence of radiant energy and especially of UV light, including photodegradation, discoloration and the like. It is unstable in the presence of light as opposed to being photostable.

The photolabile antidandruff agent in accordance with this invention is piroctone olamine.

Several antidandruff hair care products contain piroctone olamine. It is found that dissolved intact piroctone olamine molecules are the sole bioactive form of piroctone olamine. When a hair care product with piroctone olamine is utilized, the piroctone olamine dissociates and undergoes photooxidation due to which stability of the bioactive is affected which reduces its antidandruff efficacy.

Amount of the piroctone olamine in the composition of the invention would depend on the type of the hair care composition and the precise nature of other antidandruff agents used. It is preferred that the composition comprises 0.1 to 10 wt % of said photolabile antidandruff agent, more preferably 0.5 to 5 wt %, furthermore preferably 0.5 to 2 wt % by weight of the composition.

Without wishing to be bound by theory the inventors believe that the compound of the formula 1 can react with the UV radiation due to its chemical structure to prevent or reduce the destabilization of the photolabile antidandruff agent, such as piroctone olamine. Therefore, it is believed that the more the compound of the formula 1 is included in the composition, the more photolabile antidandruff agent will be stable. The the weight ratio of photolabile antidandruff agent to the compound of the formula 1 is preferably 1:0.1 to 1:10, more preferably 1:0.5 to 1:5, furthermore preferably 1:1 to 1:3.

Hair Care Composition

In accordance with a further aspect of the invention is disclosed a hair care composition of the first aspect. Preferably the composition is a shampoo, hair conditioner, hair cream, hair gel, hair serum, mousse or hair oil. More preferably the composition is a shampoo composition.

Antidandruff agents are compounds that are active against dandruff and are typically antimicrobial agents, preferably antifungal agents. Antidandruff agents typically display a minimum inhibitory concentration of about 50 mg/ml or less against *Malassezia*.

In addition to the antidandruff agent that is photolabile, the hair care composition in accordance with this invention may also comprise free additional antidandruff agent which is different from the one contained. Whenever present, the hair care composition of the invention preferably comprises 0.5 to 5 wt % of the additional antidandruff agent.

The additional antidandruff agent is preferably selected from azoles selenium sulfide, salicylic acid and combinations thereof. Azoles include ketoconazole and climbazole, preferably climbazole.

The composition of the invention especially shampoos are formulated preferably with an anionic surfactant e.g. an alkyl sulphate and/or alkoxylated alkyl sulfate surfactant. These anionic surfactants are preferably present at a level of from 2 to 16%, more preferably from 3 to 16% by weight of the composition. Preferred alkyl sulfates are C8-18 alky sulfates, more preferably C12-18 alkyl sulfates, preferably in the form of a salt with a solubilising cation such as sodium, potassium, ammonium or substituted ammonium. Examples are sodium lauryl sulfate (SLS) or sodium dodecyl sulfate (SDS).

Preferred alkyl ether sulfates are those having the formula: RO (CH2CH2O) nSO¬3M; wherein R is an alkyl or alkenyl having from 8 to 18 (preferably 12 to 18) carbon atoms; n is a number having an average value of greater than at least 0.5, preferably between 1 and 3, more preferably between 2 and 3; and M is a solubilising cation such as sodium, potassium, ammonium or substituted ammonium. An example is sodium lauryl ether sulfate (SLES).

Preferred alkoxylated alkyl sulfate anionic surfactant is sodium lauryl ether sulfate (SLES) having an average degree of ethoxylation of from 0.5 to 3, preferably 1 to 3.

The composition as per the invention optionally and preferably additionally comprises a betaine surfactant. In a preferred embodiment, the composition comprises from 0.1 to 10 wt. %, preferably from 0.5 to 8 wt. %, more preferably from 1 to 5 wt. % of a betaine surfactant, preferably an alkyl amidopropyl betaine, for example cocamidopropyl betaine.

Preferably, the hair care composition of the invention in the form of a shampoo comprise a surfactant which is sodium lauryl sulphate, sodium lauryl ether sulphate, sodium lauryl ether sulphosuccinate, ammonium lauryl sulphate, ammonium lauryl ether sulphate, sodium cocoyl isethionate and lauryl ether carboxylic acid, coco betaine, cocamidopropyl betaine, sodium cocoamphoacetate or a mixture thereof.

Preferably, the hair care composition of the present invention comprises from 1 to 50%, preferably from 2 to 40%, more preferably from 4 to 25% total surfactant.

The hair conditioning composition comprises conditioning surfactants selected from cationic surfactants, used singly or in admixture. Preferably, the cationic surfactants have the formula N+R1R2R3R4 wherein R1, R2, R3 and R4 are independently (C1 to C30) alkyl or benzyl. Preferably, one, two or three of R1, R2, R3 and R4 are independently (C4 to C30) alkyl and the other R1, R2, R3 and R4 group or groups are (C1-C6) alkyl or benzyl. More preferably, one or two of R1, R2, R3 and R4 are independently (C6 to C30) alkyl and the other R1, R2, R3 and R4 groups are (C1-C6) alkyl or benzyl groups. Optionally, the alkyl groups may comprise one or more ester (—OCO— or —COO—) and/or ether (—O—) linkages within the alkyl chain. Alkyl groups may optionally be substituted with one or more hydroxyl groups. Alkyl groups may be straight chain or branched and, for alkyl groups having 3 or more carbon atoms, cyclic. The alkyl groups may be saturated or may contain one or more carbon-carbon double bonds (eg, oleyl). Alkyl groups are optionally ethoxylated on the alkyl chain with one or more ethyleneoxy groups.

Suitable cationic surfactants for use in conditioner compositions according to the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, dihydrogenated tallow dimethyl ammonium chloride (eg, Arquad 2HT/75 from Akzo Nobel), cocotrimethylammonium chloride, PEG-2-oleammonium chloride and the corresponding hydroxides thereof. Further suitable cationic surfactants include those materials having the CTFA designations Quaternium-5, Quaternium-31 and Quaternium-18. Mixtures of any of the foregoing materials may also be suitable. A particularly useful cationic surfactant for use in conditioners according to the invention is cetyltrimethylammonium chloride, available commercially, for example as GENAMIN CTAC, ex Hoechst Celanese. Another particularly useful cationic surfactant for use in conditioners according to the invention is behenyltrimethylammonium chloride, available commercially, for example as GENAMIN KDMP, ex Clariant. Yet another preferred cationic surfactant is stearamidopropyl dimethylamine.

The most preferred cationic surfactants for use in the composition are stearamidopropyl dimethylamine, behentrimonium chloride, or stearyl trimethyl ammonium chloride. In conditioners of the invention, the level of cationic surfactant will generally range from 0.1 to 5%, preferably 0.5 to 2.5% by weight of the composition.

Hair conditioning compositions of the invention preferably may also additionally comprise a fatty alcohol. The combined use of fatty alcohols and cationic surfactants in conditioning compositions is believed to be especially advantageous, because this leads to the formation of a lamellar phase, in which the cationic surfactant is dispersed.

Representative fatty alcohols comprise from 8 to 22 carbon atoms, more preferably 16 to 22. Fatty alcohols are typically compounds containing straight chain alkyl groups. Examples of suitable fatty alcohols include cetyl alcohol, stearyl alcohol and mixtures thereof. The use of these materials is also advantageous in that they contribute to the overall conditioning properties of compositions of the invention.

The level of fatty alcohol in conditioners of the invention will generally range from 0.5 to 10%, preferably from 0.1 to 8%, more preferably from 0.2 to 7%, most preferably from 0.3 to 6% by weight of the composition. The weight ratio of cationic surfactant to fatty alcohol is suitably from 1:1 to 1:10, more preferably from 1:1.5 to 1:8, optimally from 1:2 to 1:5.

It is further preferred that the hair care composition of the invention comprises a cosmetic ingredient. Preferably the cosmetic ingredient is selected from the group consisting of a silicone, an antibacterial agent other than antidandruff agents, a foam booster, a perfume, encapsulates (for example encapsulated fragrance) a dye, a colouring agent, a pigment, a preservative, a thickener, a protein, a phosphate ester, a buffering agent, a pH adjusting agent, a pearlescer (for example; mica, titanium dioxide, titanium dioxide coated mica, ethylene glycol distearate (INCI glycol distearate)) and/or opacifier, a viscosity modifier, an emollient, a sunscreen, an emulsifier, a sensate active (for example menthol and menthol derivatives), vitamins, mineral oils, essential oils, lipids, natural actives, glycerin, natural hair nutrients such as botanical extracts, fruit extracts, sugar derivatives and amino acids, microcrystalline cellulose and mixtures thereof.

Preferably, the hair care composition of the present invention includes from 0.01 to 20 wt % of the at least one cosmetic ingredient, more preferably from 0.05 to 10 wt %, still more preferably from 0.075 to 7.5 wt % and most preferably, from 0.1 to 5 wt % of the at least one cosmetic ingredient, by weight of the total composition.

The hair care composition of the present invention may also comprise synergistic antimicrobial compounds that give synergistic antimicrobial benefit when used in combination with the antidandruff active (for example piroctone olamine) to enhance its properties and further inhibit the growth of *Malassezia furfur*. Non-limiting examples of these compounds include compounds having alcoholic groups (e.g. honokiol, magnolol or paeonol), Piperazines and a phenolic compound found in natural plant extract viz. thymol and terpeniol.

The composition may additionally comprise a vitamin B3 compound. The preferred vitamin B3 compound is niacinamide.

Niacinamide is known for secretion of AM Ps (Anti-Microbial Proteins) from keratinocytes. The AMPs thus secreted provides for improving immunity of e.g. the scalp. Thus with the use of niacinamide, the anti-dandruff efficacy can be enhanced not just through anti-fungal activity but by boosting the scalp's own protection shield against germs, through use of niacinamide. This combination could provide further long-lasting protection e.g. up to 24 hours of protection against germs.

When present, it is preferred that the hair care composition of the invention comprises 0.1 to 5% niacinamide, more preferably 0.5 to 5%, furthermore preferably 0.5 to 3%, and optimally 1.0 to 3.0% by weight of the composition.

Silicone

It is preferred that the haircare composition of the invention comprises silicone.

For example, the composition of the invention may contain emulsified droplets of a silicone conditioning agent for enhancing conditioning performance.

Suitable silicones include polydiorganosiloxanes, polydimethylsiloxanes which have the CTFA designation dimethicone. In addition, suitable for use in the compositions of the invention (particularly shampoos and conditioners) are polydimethyl siloxanes having hydroxyl end groups, which have the CTFA designation dimethiconol.

Preferably the viscosity of the emulsified silicone is at least 10,000 cst at 25° C., the viscosity of the silicone is preferably at least 60,000 cst, most preferably at least 500,000 cst, ideally at least 1,000,000 cst. Preferably the viscosity does not exceed $10^9$ cst for ease of formulation.

Examples of suitable pre-formed emulsions include Xiameter MEM 1785 and microemulsion DC2-1865 available from Dow Corning. These are emulsions/microemulsions of dimethiconol. Cross-linked silicone gums are also available in a pre-emulsified form, which is advantageous for ease of formulation. A further preferred class of silicones for inclusion in shampoos and conditioners are amino functional silicones. By "amino functional silicone" is meant a silicone containing at least one primary, secondary or tertiary amine group, or a quaternary ammonium group. Examples of suitable amino functional silicones include: polysiloxanes having the CTFA designation "amodimethicone".

Specific examples of amino functional silicones suitable for use in the invention are the aminosilicone oils DC2-8220, DC2-8166 and DC2-8566 (all ex Dow Corning). It is preferred that the total amount of silicone is 0.01 to 10% wt, more preferably 0.1 to 5 wt % and most preferably 0.5 to 3 wt %.

Shampoos

When the haircare composition of the invention is a shampoo, it is generally aqueous, i.e. they have water or an aqueous solution or a lyotropic liquid crystalline phase as their major component.

Suitably, the shampoo composition comprises 50 to 98%, preferably from 60 to 92% water.

Preferably the shampoo composition comprises one or more cationic polymers for conditioning the hair.

Suitable cationic polymers inclide homopolymers which are cationically substituted or may be formed from two or more types of monomers. The weight average ($M_w$) molecular weight of the polymers will generally be between 100000 and 3 Million Daltons. The polymers will have cationic nitrogen containing groups such as quaternary ammonium or protonated amino groups, or a mixture thereof. If the molecular weight of the polymer is too low, then the conditioning effect is poor. If too high, then there may be problems of high extensional viscosity leading to stringiness of the composition when it is poured.

The cationic nitrogen-containing group will generally be present as a substituent on a fraction of the total monomer units of the cationic polymer. Thus, when the polymer is not a homopolymer it can contain spacer non-cationic monomer units. Such polymers are described in the CTFA Cosmetic Ingredient Directory, 3rd edition. The ratio of the cationic to non-cationic monomer units is selected to give polymers having a cationic charge density in the required range, which is generally from 0.2 to 3.0 meq/gm. The cationic charge density of the polymer is suitably determined via the Kjeldahl method as described in the US Pharmacopoeia under chemical tests for nitrogen determination.

Suitable cationic polymers include copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1-C7 alkyl groups, more preferably C1-3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general, secondary and tertiary amines, especially tertiary, are preferred.

Amine substituted vinyl monomers and amines can be polymerised in the amine form and then converted to ammonium by quaternization.

The cationic polymers can comprise mixtures of monomer units derived from amine- and/or quaternary ammonium-substituted monomer and/or compatible spacer monomers.

Suitable (non-limiting examples of) cationic polymers include:
cationic diallyl quaternary ammonium-containing polymers including, for example, dimethyldiallylammonium chloride homopolymer and copolymers of acrylamide and dimethyldiallylammonium chloride, referred to in the industry (CTFA) as Polyquaternium 6 and Polyquaternium 7, respectively;
mineral acid salts of amino-alkyl esters of homo-and co-polymers of unsaturated carboxylic acids having from 3 to 5 carbon atoms, (as described in U.S. Pat. No. 4,009,256);
cationic polyacrylamides (as described in WO95/22311).

Other cationic polymers that can be used include cationic polysaccharide polymers, such as cationic cellulose derivatives, cationic starch derivatives, and cationic guar gum derivatives.

A particularly suitable type of cationic polysaccharide polymer that can be used is a cationic guar gum derivative, such as guar hydroxypropyltrimethylammonium chloride (commercially available from Rhodia in their JAGUAR trademark series). Examples of such materials are JAGUAR C13S, JAGUAR C14 and JAGUAR C17. Mixtures of any of the above cationic polymers may be used.

It is preferred that the hair care composition of the invention comprises 0.01 to 5%, preferably from 0.02 to 1%, more preferably from 0.05 to 0.8% cationic polymer.

The hair care composition of the invention may additionally comprise a cationic deposition polymer which is a cationic polygalactomannans having an average molecular weight ($M_w$) of from 1 million to 2.2 million g/mol and a cationic degree of substitution of from 0.13 to 0.3.

The polygalactomannans are polysaccharides composed principally of galactose and mannose units and are usually found in the endosperm material of seeds from leguminous plants such as guar, locust bean, honey locust, flame tree, and other members of the Leguminosae family. Polygalactomannans are composed of a backbone of 1→4-linked β-D-mannopyranosyl main chain units (also termed mannoside units or residues) with recurring 1→6-linked α-D-galactosyl side groups (also termed galactoside units or residues) branching from the number 6 carbon atom of a mannopyranose residue in the polymer backbone. The polygalactomannans of the different Leguminosae species differ from one another in the frequency of the occurrence of the galactoside side units branching from the polymannoside backbone. The mannoside and galactoside units are generically referred to herein as glycoside units or residues. The average ratio of mannoside to galactoside units in the polygalactomannan contained in guar gum (hereinafter termed "guar") is approximately 2:1.

Suitable cationic polygalactomannans include guar and hydroxyalkyl guar (for example hydroxyethyl guar or hydroxypropyl guar), that has been cationically modified by chemical reaction with one or more derivatizing agents.

In a typical composition the amount of cationic polygalactomannans will generally range from about 0.05 to 1%, preferably from 0.1 to 0.8%, more preferably 0.2 to 0.6% by weight of the composition.

The hair care composition of the invention may additionally comprise an anionic polymeric rheology modifier such as a carboxylic acid polymer.

The term "carboxylic acid polymer" in the context of this invention generally denotes a homopolymer or copolymer obtained from the polymerization of ethylenically unsaturated monomers containing pendant carboxylic acid groups (hereinafter termed "carboxylic monomers").

Suitable carboxylic monomers generally have one or two carboxylic acid groups, one carbon to carbon double bond and contain a total of from 3 to about 10 carbon atoms, more preferably from 3 to about 5 carbon atoms.

Specific examples of suitable carboxylic monomers include α-β-unsaturated monocarboxylic acids such as acrylic acid, methacrylic acid and crotonic acid; and α-β-unsaturated dicarboxylic acids such as itaconic acid, fumaric acid, maleic acid and aconitic acid. Salts, esters or anhydrides of the α-β-unsaturated mono- or dicarboxylic acids described above may also be used. Examples include half esters of α-β-unsaturated dicarboxylic acids with $C_{1-4}$ alkanols, such as monomethyl fumarate; cyclic anhydrides of α-β-unsaturated dicarboxylic acids such as maleic anhydride, itaconic anhydride and citraconic anhydride; and esters of acrylic acid or methacrylic acid with $C_{1-30}$ alkanols, such as ethyl acrylate, butyl acrylate, 2-ethylhexyl acrylate, dodecyl acrylate, hexadecyl acrylate, and octadecyl acrylate.

Optionally, other ethylenically unsaturated monomers can be copolymerized into the carboxylic acid polymer backbone. Example of such other ethylenically unsaturated monomers include styrene, vinyl acetate, ethylene, butadiene, acrylonitrile and mixtures thereof. Carboxylic acid polymers may preferably have a molecular weight of at least 1 million Daltons.

Suitable examples include crosslinked copolymers polymerized from C1-4 alkyl acrylate or methacrylate (e.g. ethyl acrylate) with one or more comonomers selected from acrylic acid, methacrylic acid and mixtures thereof. Such materials may generally be referred to under the INCI name of Acrylates Copolymer. Commercially available examples include Aculyn® 33 from Rohm and Haas.

Also suitable are crosslinked copolymers polymerized from $C_{10-30}$ alkyl esters of acrylic or methacrylic acid with one or more comonomers selected from acrylic acid, methacrylic acid and their respective $C_{1-4}$ alkyl esters. Such materials may generally be referred to under the INCI name of Acrylates/C10-30 Alkyl Acrylate Crosspolymer. Commercially available examples include Carbopol® polymers 1342 and 1382 from Lubrizol Advanced Materials.

Also suitable are optionally crosslinked copolymers of acrylic acid or methacrylic acid with alkyl acrylates and ethoxylated hydrophobically modified alkyl acrylates. Such materials may generally be referred to under the INCI names of Acrylates/Steareth-20 Methacrylate Copolymer, Acrylates/Beheneth-25 Methacrylate Copolymer, Acrylates/Steareth-20 Methacrylate Crosspolymer and Acrylates/Palmeth-25 Acrylates Copolymer. Commercially available examples include Aculyn® 22, 28 or 88 from Rohm & Haas and Synthalen® from 3V Sigma.

It is preferred that the carboxylic acid is a Carbomer, such as homopolymers of acrylic acid crosslinked with an allyl ether of pentaerythritol or an allyl ether of sucrose.

Mixtures of any of the aforementioned materials may also be used.

Preferably the hair care composition of the invention comprises 0.1 to 3.0%, more preferably 0.4 to 1.5% carboxylic acid polymer by weight of the composition.

In formulations containing anionic polymeric rheology modifiers such as the carboxylic acid polymers described above, it is often necessary to neutralize at least a portion of the free carboxyl groups by the addition of an inorganic or organic base. Examples of suitable inorganic or organic bases include alkali metal hydroxides (e.g. sodium or potassium hydroxide), sodium carbonate, ammonium hydroxide, methylamine, diethylamine, trimethylamine, monoethanolamine, triethanolamine and mixtures thereof.

The hair care composition of the invention may also comprise a nonionic polymeric rheology modifier which is selected from one or more nonionic cellulose ethers.

Suitable nonionic cellulose ethers or use as the nonionic polymeric rheology modifier in the invention include ($C_{1-3}$ alkyl) cellulose ethers, such as methyl cellulose and ethyl cellulose; hydroxy ($C_{1-3}$ alkyl) cellulose ethers, such as hydroxyethyl cellulose and hydroxypropyl cellulose; mixed hydroxy ($C_{1-3}$ alkyl) cellulose ethers, such as hydroxyethyl hydroxypropyl cellulose; and ($C_{1-3}$ alkyl) hydroxy ($C_{1-3}$ alkyl) cellulose ethers, such as hydroxyethyl methylcellulose and hydroxypropyl methylcellulose.

Preferred nonionic cellulose ethers for use as the nonionic polymeric rheology modifier in the invention are water-soluble nonionic cellulose ethers such as methylcellulose and hydroxypropyl methylcellulose. The term "water-soluble" in this context denotes a solubility in water of at least 1 gram, more preferably at least 3 grams, most preferably at least 5 grams in 100 grams of distilled water at 25° C. and 1 atmosphere. This level indicates production of a macroscopically isotropic or transparent, coloured or colourless solution.

Methyl cellulose and hydroxypropyl methylcellulose are commercially available in a number of viscosity grades from Dow Chemical as their METHOCEL® trademark series.

Mixtures of any nonionic cellulose ethers may also be suitable. In a typical composition according to the invention the level of nonionic cellulose ethers will generally range from about 0.01 to about 2.0%, and preferably ranges from 0.1 to 0.5%, more preferably from 0.1 to 0.3%, by weight based on the total weight of the composition.

Preferably the haircare composition of the invention comprises 0.1 to 0.3% by weight nonionic cellulose ether.

The hair care composition of the invention may contain further optional ingredients to enhance performance and/or consumer acceptability. Examples of such ingredients include fragrance, dyes and pigments and preservatives. Each of these ingredients will be present in an amount effective to accomplish its purpose. Generally, these optional ingredients are included individually at a level of up to 5% by weight based on the total weight of the composition.

Method and Use

The present invention also provides for a non-therapeutic method of treating dandruff comprising a step of applying thereon a composition of the first aspect. Preferably it is for cosmetic purpose.

The present invention also provides for use of a composition of the first aspect to treat a dandruff. In one aspect the use is non-therapeutic in nature, preferably cosmetic in nature.

Mode of Use

The hair care composition of the invention is primarily intended for topical application to hair and scalp.

When the composition is a shampoo, it is topically applied to the hair and then massaged into the hair and scalp. Then it is rinsed with water prior to drying the hair. A hair oil or hair serum, being leave-on hair care compositions, are left on for 1 to 10 hours after application before being washed off.

The invention will be further illustrated by the following, non-limiting Examples, in which all percentages quoted are by weight based on total weight unless otherwise stated.

The examples are intended to illustrate the invention and are not intended to limit the invention to those examples per se.

EXAMPLES

Example 1

Preparation of a Compound of the Formula 1

The compound of formula 1 used in the experiments was prepared using the following materials, methods and procedures:

UV Treatment:

0.05 g Octopirox® was dissolved in 10 ml methanol in a transparent glass vial. The UV irradiation was carried out in an X-Rite® (Macbeth) Spectra Light III chamber. UV mode was chosen for UV irradiation which provides both UVA and UVB lights. The UV light was tested by the UVX Radiometer (UVX-36, E24195, UVP.) and the intensity was estimated at 250 μw/cm$^2$ for UVA and 110 μw/cm$^2$ for UVB). The chamber temperature was equal to the room temperature (20±2° C.). The samples were placed in a line close to the center of the chamber. After 6 hours, the sample was concentrated by a rotary evaporator.

Separation:

The mixture of UV degradation products so formed upon exposure of the compound of the formula 1 to UV light was firstly concentrated by a rotary evaporator. The separation was carried out with a silica gel column (2×48 cm, V=150 mL) filled with 60 g silica gel (200-300 mesh size). The silica gel column was activated and balanced by petroleum ether/ethyl acetate (2/1, v/v). After added to the silica gel column, the concentrated mixture of UV degradation products was separated by the gradient elution with a speed at 6 mL/minute. Then the compound inside the invention was collected by evaporating the solvent with rotary evaporator.

Element analysis, IR, MS and NMR analysis were used to confirm the chemical structure of the compound, which is:

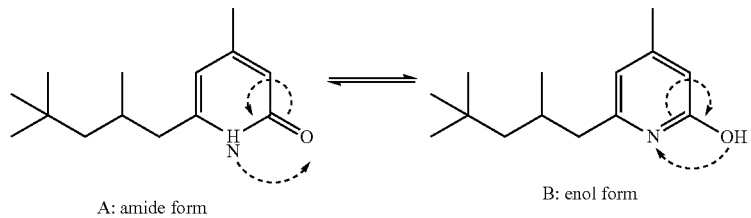

A: amide form    B: enol form

The amide form dominates when the pH is below 7, and it is enol form dominates when the pH is greater than 7.

Preparation of a Hair Care Composition

The following compositions having specific combination of Octopirox® and the compound inside the invention as shown in Table 1 were prepared. The pH of the composition was adjusted respectively by either adding formic acid or ammonia.

TABLE 1

| Composition Ref. No. | Octopirox®/ wt % | The compound of formula 1/wt % | pH of the medium | Methanol wt % |
|---|---|---|---|---|
| A | 0.002 | 0 | 4 | To 100 |
| 1 | 0.002 | 0.002 | 4 | To 100 |
| 2 | 0.002 | 0.004 | 4 | To 100 |
| 3 | 0.002 | 0.010 | 4 | To 100 |
| B | 0.002 | 0 | 10 | To 100 |
| 4 | 0.002 | 0.002 | 10 | To 100 |
| 5 | 0.002 | 0.004 | 10 | To 100 |
| 6 | 0.002 | 0.010 | 10 | To 100 |

The compositions/ingredients shown in Table 1 above were subjected to an experiment that gives an estimate of the residual amount of Octopirox® in the hair care composition after being exposed to UV light for a long time. The % average residual amount of Octopirox® was measured using an invitro model which is described hereinafter.

Test to Determine UV Stability of the Composition

The test conditions are described hereinbelow.

The UV irradiation was carried out in an X-Rite (Macbeth) Spectra Light III chamber. UV mode was chosen for UV irradiation which provides both UVA and UVB lights. The UV light was tested by the UVX Radiometer (UVX-36, E24195, UVP.) and the intensity was estimated at 250 µw/cm² for UVA and 110 µw/cm² for UVB). The chamber temperature was equal to the room temperature (20±2° C.). The samples were placed in a line close to the center of the chamber.

Procedure

Each sample was placed under UV cabinet (Macbeth SpectraLight III) at 37° C. for 120 minutes of exposure, then transferred to a Liquid Chromatography sample vial for analysis of Octopirox® by UPLC-UV analysis.

A Waters® ACQUITY ultra performance liquid chromatography ((Waters, Manchester, UK) was used for the sample analysis. MassLynx software (version 4.1) was used for instrument control and data acquisition. Separation was carried out on a Waters Acquity UPLC BEH C18 column (2.1×50 mm, 1.7 µm particle size). The mobile phase A was composed of 0.1% formic acid in DI water and the mobile phase B was composed of 0.1% formic acid in acetonitrile, programmed in a gradient mode. The sample was measured by PDA detector at absorption wavelength of 302 nm.

The observations are summarised in Table 2.

TABLE 2

| Composition Ref. No. | Details | % average[1] residue of octopirox® | SD[2] |
|---|---|---|---|
| A | Octopirox®; pH = 4 | 18.1 | 2.8 |
| 1 | Octopirox® + the compound[3] (ratio = 1:1); pH = 4 | 38.5 | 2.6 |
| 2 | Octopirox® + the compound (ratio = 1:2); pH = 4 | 46.1 | 3.2 |
| 3 | Octopirox® + the compound (ratio = 1:5); pH = 4 | 58.9 | 0.6 |
| B | Octopirox®; pH = 10 | 33.0 | 5.2 |
| 4 | Octopirox® + the compound (ratio = 1:1); pH = 10 | 45.0 | 3.0 |
| 5 | Octopirox® + the compound (ratio = 1:2); pH = 10 | 50.4 | 3.6 |
| 6 | Octopirox® + the compound (ratio = 1:5); pH = 10 | 61.8 | 2.4 |

[1]Indicates the average of two readings
[2]SD is the standard deviation of the % average residue
[3]The compound means compound of the formula 1

The data contained in Table 2 clearly indicates that stability of piroctone olamine improves markedly when the composition in accordance with this invention is used (Compositions 1-6) during the experiments, as compared to a corresponding example outside the invention (Compositions A and B, not containing the compound of the formula 1). The data further indicates that the role of compound of the formula 1 in improving the UV-stability of photolabile antidandruff agents such as piroctone olamine has now been demonstrated. The data also indicates that either amide form or enol form of the compound of formula 1 is effective for improving the UV-stability of photolabile antidandruff agents.

Octopirox® Degradation Under Cool White Light

Cool White Light Treatment:

The cool white light (CWL) irradiation was carried out in an X-Rite (Macbeth) Spectra Light III chamber. CWL mode was chosen which provides stable irradiation mimicking the indoor light. The intensity of light was fixed which estimated at 6 µw/cm2 for UVA and 1.5 µw/cm² for UVB). The chamber temperature was equal to the room temperature (20±2° C.). The sample was placed in a line close to the center of the chamber. After 24 hours, the sample was analyzed by LCMS (Water UPLC coupled with Quatro Micro MS), by quantitatively measured using UPLC-UV analysis following DPS derivatization.

The separation was performed by a UPLC BEH C18 column and the mobile phase was acetonitrile/water (60/40, 0.1% formic acid) in isocratic elution. Electrospray ionization in positive mode was applied for MS scan.

It is found that the quantity of Octopirox® is reduced, therefore indicating the degradation of Octopirox® happens under the cool white light. However, there's no compound of formula 1 can be detected in the degradation product. It can be concluded that there's no compound of formula 1 after exposing the Octopirox® under cool white light (indoor light) for long time. The preparation of the compound of formula 1 requires exposure of Octopirox® under strong UV radiation for sufficient time, which differs from the storage condition of Octopirox®.

The invention claimed is:

1. A hair care composition comprising:
   (i) a compound of the formula 1, which may exist in amide form A or enol form B;

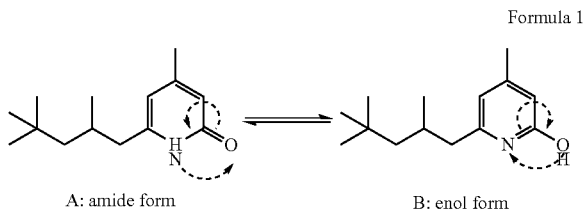 [SMILES: Cc1cc(CC(C)CC(C)(C)C)[nH]c(=O)c1 ; Cc1cc(O)nc(CC(C)CC(C)(C)C)c1]

Formula 1

A: amide form      B: enol form (ii) a photolabile antidandruff agent; and
   (iii) a cosmetically acceptable carrier; wherein said photolabile antidandruff agent is piroctone olamine.

2. The hair care composition as claimed in claim 1 wherein the weight ratio of said photolabile antidandruff agent to said compound of formula 1 is from 1:0.1 to 1:10.

3. The hair care composition as claimed in claim 1 wherein amount of said photolabile antidandruff agent is 0.1 to 10 wt %.

4. The hair care composition as claimed in claim 1 wherein amount of said compound of formula 1 is 0.01 to 10 wt %.

5. The hair care composition as claimed in claim 1 additionally comprising a surfactant.

6. The hair care composition as claimed in claim 5 wherein the surfactant is an anionic surfactant or a cationic surfactant.

7. The hair care composition as claimed in claim 6 wherein the anionic surfactant is an alkyl sulphate and/or an alkoxylated alkyl sulfate surfactant.

8. The hair care composition as claimed in 7 wherein said composition further comprises a betaine surfactant.

9. The hair care composition as claimed in claim 5 wherein the composition is a shampoo.

10. The hair care composition as claimed in claim 6 wherein the cationic surfactant is stearamidopropyl dimethylamine, behentrimonium chloride, or stearyl trimethyl ammonium chloride.

11. The hair care composition as claimed in claim 10 wherein said composition further comprises 0.5 to 10 wt % of a fatty alcohol.

12. The hair care composition as claimed in claim 10 wherein the composition is a hair conditioner.

13. A method of treating or reducing dandruff comprising a step of applying thereon the composition as claimed in claim 1.

* * * * *